(12) United States Patent
Lewis-Gray

(10) Patent No.: US 11,506,582 B2
(45) Date of Patent: Nov. 22, 2022

(54) SENSOR SYSTEM

(71) Applicant: GEKKO SYSTEMS PTY LTD, Ballarat (AU)

(72) Inventor: Alexander Hamilton Lewis-Gray, Ballarat (AU)

(73) Assignee: GEKKO SYSTEMS PTY LTD

( * ) Notice: Subject to any disclaimer, the term of this patent is extended or adjusted under 35 U.S.C. 154(b) by 233 days.

(21) Appl. No.: 16/635,564

(22) PCT Filed: Aug. 2, 2018

(86) PCT No.: PCT/AU2018/000126
§ 371 (c)(1),
(2) Date: Jan. 31, 2020

(87) PCT Pub. No.: WO2019/023735
PCT Pub. Date: Feb. 7, 2019

(65) Prior Publication Data
US 2020/0166441 A1   May 28, 2020

(30) Foreign Application Priority Data
Aug. 2, 2017   (AU) ............................... 2017903061

(51) Int. Cl.
*G01N 1/40* (2006.01)
*C22B 11/00* (2006.01)
(Continued)

(52) U.S. Cl.
CPC ............. *G01N 1/4077* (2013.01); *C22B 3/24* (2013.01); *C22B 11/04* (2013.01); *G01N 23/223* (2013.01);
(Continued)

(58) Field of Classification Search
CPC ......... G01N 1/4077; G01N 2001/4088; G01N 23/223; C22B 11/04; C22B 3/44
See application file for complete search history.

(56) References Cited

U.S. PATENT DOCUMENTS

2018/0223389 A1\* 8/2018 McGrath .............. G01N 1/4077

FOREIGN PATENT DOCUMENTS

WO     WO 2017008097      1/2017

\* cited by examiner

*Primary Examiner* — Don K Wong
(74) *Attorney, Agent, or Firm* — Galbreath Law Offices, P.C.; John A. Galbreath

(57) ABSTRACT

Contemplated is a sensor system for use with a measuring device. The measuring device being of the type adapted to measure the volume of a desired solid component in a sample volume of a solid-liquid slurry obtained from either a carbon-in-pulp or carbon-in-leach process. The solid-liquid slurry comprises granular carbon particles, ore pulp, and water. The carbon-in-pulp or carbon-in-leach process includes at least one retention tank. The measurement device including: a receptacle for receiving the sample volume of the slurry; a screen provided in the receptacle for separating out the desired solid component from a remainder of the slurry. The solid component is retained in the receptacle to form a bed therein and the remainder is exhausted from the receptacle. The sensor system measures in either the retained solid component, or the exhausted remainder, or both one of: pH; dissolved oxygen; pulp density or carbon content.

6 Claims, 3 Drawing Sheets

(51) Int. Cl.
 *G01N 23/223* (2006.01)
 *C22B 3/24* (2006.01)
 *C22B 3/44* (2006.01)
(52) U.S. Cl.
 CPC ........ *C22B 3/44* (2013.01); *G01N 2001/4088* (2013.01)

SENSOR SYSTEM

FIELD OF THE INVENTION

The present invention relates to mineral ore processing equipment, and in particular to a sensor and control system for a measuring apparatus used in a mineral processing process.

BACKGROUND OF THE INVENTION

A measuring apparatus for use in a carbon-in-pulp or carbon-in-leach process is disclosed in patent application WO2017008097. The measuring apparatus is used to sample a slurry and determine the volume and/or mass of carbon particles it contains. This information is used to control the retention time of the carbon within one of more retention vessels. If the time in the vessel is too long, then the process is not running at its peak efficiency, and if the retention is not long enough, then valuable ore is lost to the waste product associated with the process.

The speed, variety, and accuracy of the parameters that indicate the status of the standardised sample are critical in ensuring that the process is operating at peak efficiency and profitability.

The present invention improves upon the initial inventive disclosure and improves at least some of the parameters sensed and helps make more informed decisions regarding the continuous operation of the process.

DISCLOSURE OF THE INVENTION

Accordingly, the present invention is a sensor system for use with a measuring device. The measuring device being of the type adapted to measure the volume of a desired solid component in a sample volume of a solid-liquid slurry obtained from either a carbon-in-pulp or carbon-in-leach process. The solid-liquid slurry comprises granular carbon particles, ore pulp, and water. The carbon-in-pulp or carbon-in-leach process includes at least one retention tank. The measurement device including:
  a receptacle for receiving the sample volume of the slurry;
  a screen provided in the receptacle for separating out the desired solid component from a remainder of the slurry.

After initial collection of a sample, the solid and liquid components are separated. The solid component is retained in the receptacle to form a bed therein and the remainder is exhausted from the receptacle. The sensor system is adapted to measure at least one of the following parameters, in either the, collected sample, retained solid component, or the exhausted remainder, or both:
  a) pH (Potential Hydrogen)
  b) Dissolved oxygen
  c) Pulp density
  d) Gold or other elemental content, in either the solid material or the solution, without direct physical contact with either.

Preferably, at least one pH probe is included, and adapted to sense the pH level of the sample collected in the receptacle.

Optionally, at least one additional pH probe is included, and adapted to sense the pH of the exhausted remainder.

Preferably, at least one dissolved oxygen probe is included, and adapted to sense the dissolved oxygen of the contents of the receptacle.

Optionally, at least one additional dissolved oxygen probe is included, and adapted to sense the dissolved oxygen of the exhausted remainder.

Optionally, the outputs from the plurality of dissolved oxygen probes are received by a logic control means that is adapted to determine the differential, if any, between the dissolved oxygen within the receptacle, and the dissolved oxygen of the exhausted remainder.

Preferably, at least one weighing means is included, and adapted to determine the weight of the contents of the receptacle, which includes a known volume, so that the density of the contents can be determined.

Preferably, an X-ray emitter and receiver means is included and adapted to emit a beam of X-rays, either continuously, or in bursts, into the bed of solids retained in the receptacle, and the receiver means is adapted to receive and measure the amount of characteristic secondary X-rays generated by the interaction of the bed of solids and the X-ray beam due to X-ray fluorescence. This technique can then be used to determine the amount of a specific element(s) contained in the bed of solids. One particular application of this would be to determine the amount of gold absorbed onto carbon another would be to look for elements which effect the process.

Optionally, either the entire bed of solids, or a suitable sample of the bed of solids, is first removed from the retaining vessel, prior to subjected to the X-ray emitter and receiver means.

Preferably, the output from the sensor system is fed back to a control system or an operator, and the control system utilises logic control means, in association with the derived data from the sensor system, to monitor and control critical operational parameters of the carbon-in-pulp, or carbon-in-leach process, to maximise its operational efficiency. The gold on carbon measurement can also be used to account for gold content throughout the circuit and also optimise downstream processes such as the recovery of gold from the carbon.

Preferably, the one or more measured parameters are used to determine the parts per million of retained gold within the granular carbon particles.

Preferably, the one or more measured parameters are used to determine the density of the extracted slurry to determine if it is within the range required for a homogenous distribution of carbon throughout the tank.

Preferably, the control system controls at least the period of time that the slurry is retained within one of the at least one retention tanks, to ensure that optimal adsorption of gold into the carbon particles is achieved.

In another aspect of the invention, there is provided a method of monitoring and controlling the operation of either a carbon-in-pulp or a carbon-in-leach process. The method includes the steps of:
  a) retaining a sample volume sized quantity of a slurry, and then
  b) screening out and retaining a measured amount of solid material, predominately made up of carbon particles, from the sample volume sized quantity of slurry, and then
  c) exhausting the remainder of slurry from the sample volume sized quantity of slurry, and then
  d) using a sensor system to determine at least one, of a plurality of parameters, of either the volume sized quantity of the sample, the retained solid portion of the sample, or the exhausted slurry portion, or both, wherein the parameters measured by the sensor system include:

pH (Potential Hydrogen)

Dissolved oxygen

Pulp density

Elements such as Gold content, in either the solid material or the solution, without direct physical contact with either, to determine the parts per million of retained elements such as gold within the granular carbon particles.

Preferably, the method may include the further step:

e) of using an X-ray emitter and associated sensor that is adapted to detect "secondary" X-rays emitted by either the measured amount of retained solid material solid, or the exhausted slurry portion, due to X-ray fluorescence.

Preferably, the method may include the further step of:

f) feeding the data derived from the sensor system to a logic control means that are capable of monitoring and controlling the carbon-in-pulp or carbon-in-leach process, and thereby determine an optimal retention time within any adsorption tank within either the carbon-in-pulp or carbon-in-leach process.

DESCRIPTION OF THE PREFERRED EMBODIMENTS

Figure 1:
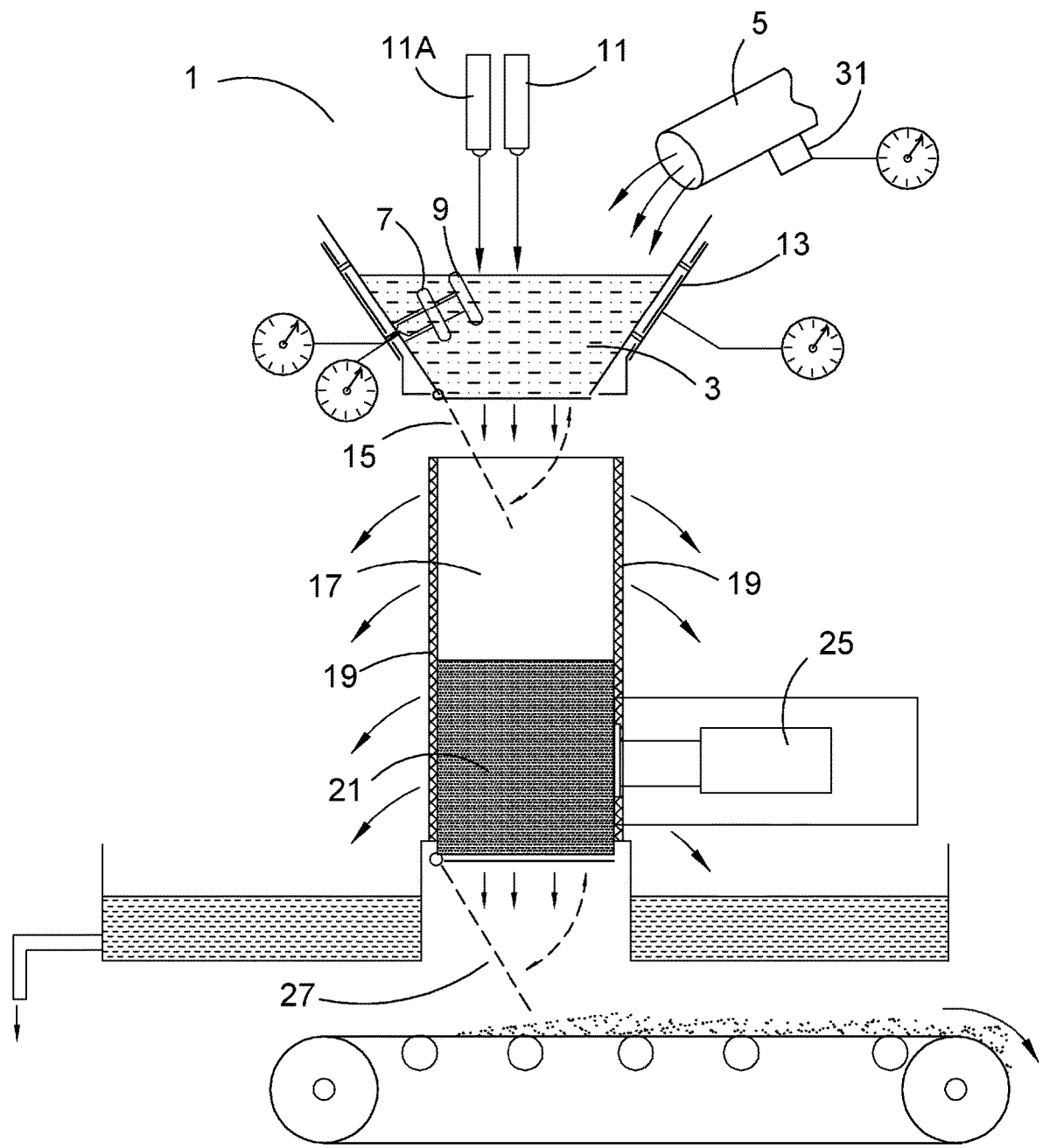
FIG. 1 is a schematic diagram of one form of the present invention.

Turning firstly to FIG. 1, we are shown a schematic diagram of one preferred form of the present invention in which there is a sensor and control system 1 included in a measuring device incorporated in a carbon-in-pulp or carbon-in-leach process that has at least one retention tank. The particles of carbon, ore, and gangue are incorporated into a slurry that is fed into the measuring device via slurry outlet 5 into a first vessel 3. The first vessel 3 includes a number of sensors and other measuring apparatus, including a pH sensor 7 and a dissolved oxygen sensor 9. The emitter and receiver sensor 11A is used to measure the depth of the slurry in the first vessel 3. Alternatively, a set volume of slurry in let into vessel 3. A set of scales 13 are also included with the first vessel 3 and is adapted to weigh the slurry sample in the vessel 3. The weight and volume can then be combined to determine the density of the sample. An alternate to this the fitment of the density detector to the slurry feed line that becomes outlet 5.

After the first set of readings from the variety of sensors are completed, flap 15 opens to allow the slurry sample to drop down into the second retention vessel 17. The second retention vessel 17 includes screens 19 that allow the liquid part of the slurry to drain away, leaving only the retained solid portion 21. An X-ray beam emitter and X-ray fluorescence detector means 25 emits a beam of X-rays into the retained solid portion 21. The interaction of the beam upon the retained solid particles causes X-ray fluorescence, which is then detected by the detector means portion of 25. An additional measurement can also be made. With flap 15 still open, the laser is also used to measure the height of the retained solids and using the known dimensions of the retention vessel 17, this is converted into a volume of retained solids. Once these readings have been obtained, the flap 27 opens, allowing the retained solid portion 21 to exit the apparatus.

Figure 2:
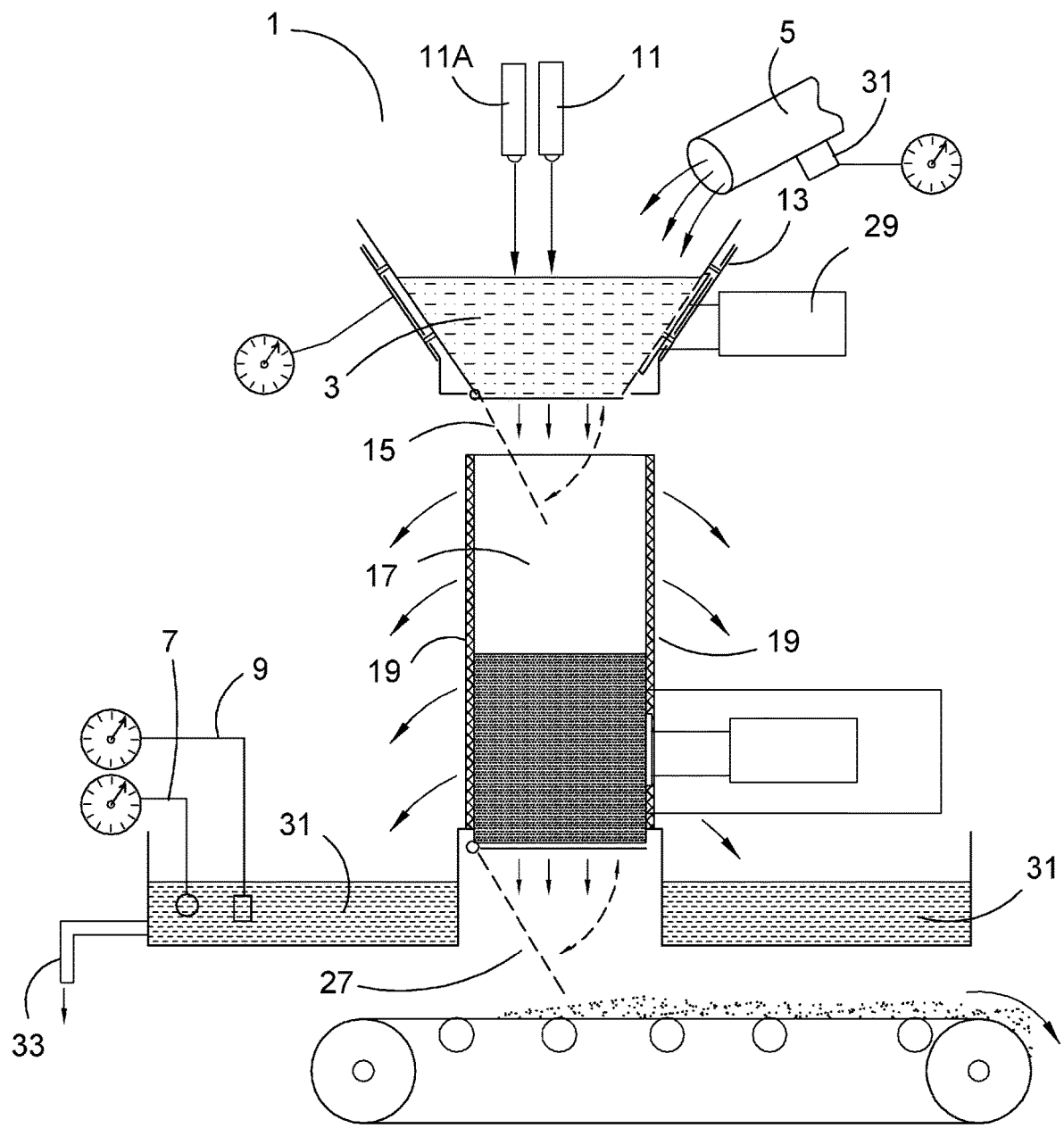
FIG. 2 is a schematic diagram of another form of the present invention.

FIG. 2 shows an alternative preferred embodiment for the present invention. In this view, we can see the sensor and control system 1 is incorporated into the sampling and measuring apparatus in a different arrangement. The slurry is fed into the first vessel 3 via the slurry outlet 5. The depth of the slurry contained in the first vessel 3 is measured by an emitter and receiver sensor 11A. Alternatively, a set volume of slurry in let into vessel 3 The weight of the slurry sample retained in the first vessel 3 is measured via the scales 13. In this embodiment, a second X-ray beam emitter and X-ray fluorescence detector means 29 is included in the first vessel 3. Just like the first embodiment, the X-ray beam emitter and X-ray fluorescence detector means 29 emits a beam of X-rays into the slurry and is adapted to measure the X-ray fluorescence the beam creates via its interaction with the slurry.

15 opens, thereby allowing the slurry sample to drop into the second retention vessel 17. The second vessel 17 incorporates screens 19 which allow the liquid part of the slurry to drain away, leaving behind only the retained solid portion 21. The X-ray beam emitter and X-ray fluorescence detector means 25 then measure the fluorescence generated within the retained solid portion. An additional measurement can also be made. With flap 15 still open, the laser is also used to measure the height of the retained solids and using the known dimensions of the retention vessel 17, this is converted into a volume of retained solids. Once these readings have been made, flap 27 opens, thereby allowing the retained solids portion 21 to exit the second retention vessel 17.

The drained liquid portion of the slurry is retained in a third retention vessel 31. A pH sensor 7 and a dissolved oxygen sensor 9 measure these parameters in the drained liquid. The liquid portion is then drained from the third retention vessel 31 via spigot 33.

Figure 3:
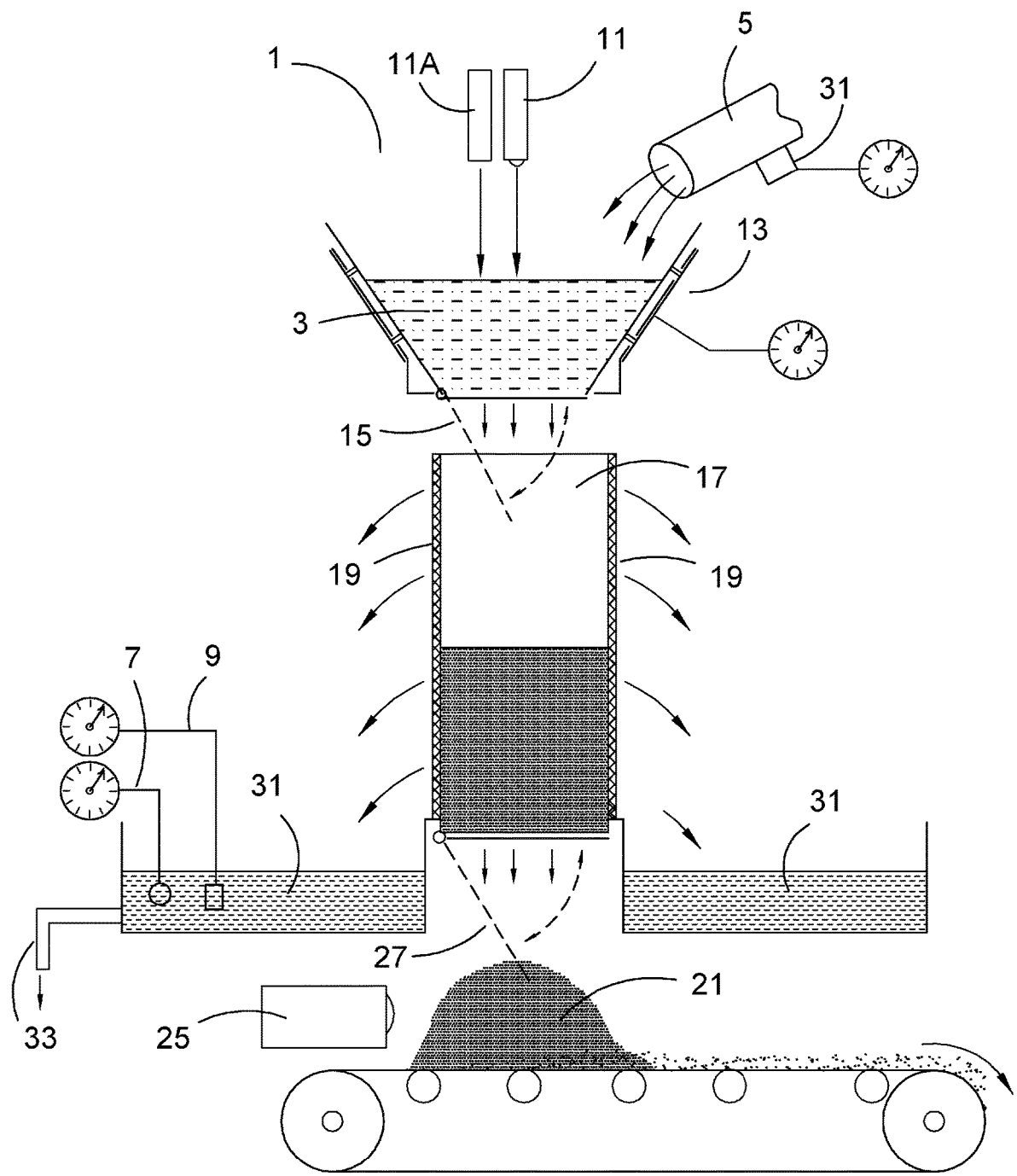
FIG. 3 is a schematic diagram of another form of the present invention.

Turning to FIG. 3, we are shown yet another variation of the preferred embodiment. In this embodiment, the retained solid portion 21 is dumped into a heap, after the liquid has been drained away in the second retention vessel 17, and the X-ray beam emitter and X-ray fluorescence detector means 25 operates upon the heap. This arrangement mitigates any affect that the screen 19 of the second retention vessel 17 may have on the effectiveness or efficiency of either the X-ray emitter and/or the X-ray fluorescence detector.

While the above description includes the preferred embodiments of the invention, it is to be understood that many variations, alterations, modifications and/or additions may be introduced into the constructions and arrangements of parts previously described without departing from the essential features or the spirit or ambit of the invention.

It will be also understood that where the word "comprise", and variations such as "comprises" and "comprising", are used in this specification, unless the context requires otherwise such use is intended to imply the inclusion of a stated feature or features but is not to be taken as excluding the presence of other feature or features.

The reference to any prior art in this specification is not, and should not be taken as, an acknowledgment or any form of suggestion that such prior art forms part of the common general knowledge.

The invention claimed is:

1. A sensor system for use with a measuring device, said measuring device being of the type adapted to measure the volume of a desired solid in component in a sample volume of a solid-liquid slurry obtained from either a carbon-in-pulp or carbon-in-leach process and said solid-liquid slurry comprises granular carbon particles, ore pulp, and water, said carbon-in-pulp or carbon-in-leach process including at least one retention tank, the measurement apparatus including:
- a receptacle for receiving the sample volume of the slurry;
- a screen provided in the receptacle for separating out the desired solid component from a remainder of the slurry, wherein the solid component is retained in the receptacle to form a bed therein and the remainder is exhausted from the receptacle; and wherein said sensor system is adapted to measure at least one of the following parameters in either the retained solid component, or the exhausted remainder, or both:
  - a) pH (Potential Hydrogen)
  - b) Dissolved oxygen
  - c) Pulp density
  - d) Carbon content, in either the solid material or the solution, without direct physical contact with either;

and wherein the sensor system used to determine the carbon content includes an X-ray emitter and at least one X-Ray detector adapted to measure the characteristic "secondary" X-rays emitted from either the solid material or the solution due to X-ray fluorescence;

and wherein the output from the sensor system is fed back to a control system, said control system utilising logic control means in association with the derived data from the sensor system to monitor and control critical operational parameters of the carbon-in-pulp or carbon-in-leach process to maximise its operational efficiency.

2. The sensor system as defined in claim 1 wherein the one or more measured parameters are used to determine the parts per million of retained gold within the granular carbon particles.

3. The sensor system as defined in claim 2 wherein the control system controls the period of time that the slurry is retained within one of the at least one retention tanks to ensure peak absorption of gold into the carbon particles is achieved.

4. According to a further aspect of the invention, there is provided a method of monitoring and controlling the operation of either a carbon-in-pulp or a carbon-in-leach process, said method including the steps of:
  - a) retaining a sample volume sized quantity of a slurry, and then
  - b) screening out and retaining a measured amount of solid material, predominately made up of carbon particles, from the sample volume sized quantity of slurry, and then
  - c) exhausting the remainder of slurry from the sample volume sized quantity of slurry, and then
  - d) using a sensor system to determine at least one, of a plurality of parameters, of either the retained solid portion of the sample volume sized quantity, or the exhausted slurry portion, or both, wherein the parameters measured by the sensor system include:
    pH (Potential Hydrogen)
    Dissolved oxygen
    Pulp density
    Carbon content, in either the solid material or the solution, without direct physical contact with either, to determine the parts per million of retained gold within the granular carbon particles.

5. The method as defined in claim 4 wherein the method may include the further step:
  - e) of using an X-ray emitter and associated sensor that is adapted to detect "secondary" X-rays emitted by either the measured amount of retained solid material solid, or the exhausted slurry portion, due to X-ray fluorescence.

6. The method as defined in claim 5 wherein the method may include the further step of:
  - f) feeding the data derived from the sensor system to a logic control means that are capable of monitoring and controlling the carbon-in-pulp or carbon-in-leach process, and thereby determine an optimal retention time within any adsorption tank within either the carbon-in-pulp or carbon-in-leach process.

* * * * *